(12) United States Patent
Arkles et al.

(10) Patent No.: US 9,358,200 B2
(45) Date of Patent: Jun. 7, 2016

(54) ALKOXYSILANE DERIVATIVES OF N-ACYL AMINO ACIDS, N-ACYL DIPEPTIDES, AND N-ACYL TRIPEPTIDES, AND PARTICLES AND STABLE OIL-IN-WATER FORMULATIONS USING THE SAME

(75) Inventors: Barry C. Arkles, Pipersville, PA (US); Jane C. Hollenberg, Red Hook, NY (US); Youlin Pan, Langhorne, PA (US)

(73) Assignee: Gelest Technologies, Inc., Morrisville, PA (US)

( * ) Notice: Subject to any disclaimer, the term of this patent is extended or adjusted under 35 U.S.C. 154(b) by 66 days.

(21) Appl. No.: 13/241,860

(22) Filed: Sep. 23, 2011

(65) Prior Publication Data

US 2012/0076840 A1   Mar. 29, 2012

Related U.S. Application Data

(60) Provisional application No. 61/385,790, filed on Sep. 23, 2010.

(51) Int. Cl.
| | |
|---|---|
| A61Q 1/02 | (2006.01) |
| C07K 5/06 | (2006.01) |
| C07C 229/02 | (2006.01) |
| A61K 8/02 | (2006.01) |
| C07K 5/08 | (2006.01) |
| A61K 8/64 | (2006.01) |
| A61K 8/19 | (2006.01) |
| A61K 8/26 | (2006.01) |
| A61K 8/29 | (2006.01) |
| A61K 8/58 | (2006.01) |
| A61Q 1/10 | (2006.01) |
| A61Q 1/12 | (2006.01) |
| C07K 5/062 | (2006.01) |
| C07K 5/083 | (2006.01) |
| C09C 1/36 | (2006.01) |
| C09C 3/12 | (2006.01) |

(52) U.S. Cl.
CPC ............... *A61K 8/64* (2013.01); *A61K 8/0241* (2013.01); *A61K 8/19* (2013.01); *A61K 8/26* (2013.01); *A61K 8/29* (2013.01); *A61K 8/585* (2013.01); *A61Q 1/02* (2013.01); *A61Q 1/10* (2013.01); *A61Q 1/12* (2013.01); *C07K 5/06026* (2013.01); *C07K 5/0806* (2013.01); *C09C 1/3684* (2013.01); *C09C 3/12* (2013.01); *A61K 2800/623* (2013.01); *C01P 2004/61* (2013.01); *C01P 2004/62* (2013.01)

(58) Field of Classification Search
None
See application file for complete search history.

(56) References Cited

U.S. PATENT DOCUMENTS

| | | | | |
|---|---|---|---|---|
| 2,929,829 | A * | 3/1960 | Morchouse | .................... 556/419 |
| 3,652,761 | A | 3/1972 | Weetall | |
| 4,606,914 | A | 8/1986 | Miyoshi | |
| 5,149,426 | A * | 9/1992 | Watabe et al. | ............. 210/198.2 |
| 5,326,392 | A | 7/1994 | Miller et al. | |
| 7,374,783 | B2 | 5/2008 | Hasegawa et al. | |
| 2006/0024375 | A1* | 2/2006 | Hasegawa et al. | ............ 424/489 |
| 2009/0220449 | A1 | 9/2009 | Wilson et al. | |

FOREIGN PATENT DOCUMENTS

| | | |
|---|---|---|
| EP | 0637902 A1 | 2/1995 |
| JP | 2002-146011 A | 5/2002 |
| JP | 2007-170064 A | 7/2007 |
| JP | 2009-526405 A | 7/2009 |

OTHER PUBLICATIONS

ARKLES: "Tailoring surfaces with silanes", Chemtech, 7, pp. 766-778 (1977).
Search Report issued Feb. 20, 2014 in FR Application No. 1158480.
Engelhardt et al, "Chemically bonded stationary phases for aqueous high-performance exclusion chromatography," Journal of Chromatography, vol. 142, pp. 311-320 (1977).
Office Action issued Sep. 15, 2015 in JP Application No. P2011-209534.

* cited by examiner

*Primary Examiner* — Bethany Barham
*Assistant Examiner* — Melissa Javier
(74) *Attorney, Agent, or Firm* — Panitch Schwarze Belisario & Nadel LLP

(57) ABSTRACT

Hydrophilic N-acylamino acid, N-acyl dipeptide, and N-acyl tripeptide substituted silanes are prepared which can be utilized as reactive surface treatments for particles of pigments, minerals, and fillers. These treated particles form stable dispersions in the aqueous phase of oil-in-water mixtures that are suitable for cosmetic applications. The treated particles may also be used in pressed powder and color cosmetic formulations.

11 Claims, No Drawings

ALKOXYSILANE DERIVATIVES OF N-ACYL AMINO ACIDS, N-ACYL DIPEPTIDES, AND N-ACYL TRIPEPTIDES, AND PARTICLES AND STABLE OIL-IN-WATER FORMULATIONS USING THE SAME

CROSS-REFERENCE TO RELATED APPLICATIONS

This application claims the benefit of U.S. provisional patent Application No. 61/385,790, filed on Sep. 23, 2010, the disclosure of which is incorporated herein by reference.

BACKGROUND OF THE INVENTION

Surface treated pigments have been used to improve the wetting and dispersion of pigments and fillers in inks, coatings, resins and cosmetics. Passivation of the pigment and filler surfaces to reduce chemical interaction with the vehicle is another application of surface modifications. In cosmetics, surface coatings of pigments and fillers offer the added benefits of improvements in skin feel, easier spreading and blending on the skin, reduction in irritation due to mechanical abrasion and reduced drying of the skin from oil and moisture absorption.

Types of surface coatings used in cosmetic applications have included fatty acids, lecithin, mineral waxes, e.g. polyethylene, vegetable waxes, starches, peptides, polysaccharides, acyl amino acids, titanate esters, fluorophosphates, silicones and silanes. The modification of substrates with silanes is well-known in the art and is described by Arkles in *Chemtech,* 7(12), 766, (1977), which is herein incorporated by reference. Silane coupling agents and reactive silicones are particularly useful surface treatments for use in dispersed systems due to the formation of chemical bonds between the treating compound and the pigment surface that prevents solubilization of the coating during processing of the finished product. Silane and silicone surface treated pigments have been used in a variety of cosmetic formulations, including foundation, mascara, eye liner, eye shadow, lip color and blush, in which the powder is dispersed in a liquid phase. The most common hydrophilic silane utilized is $PEG_{6-9}$-silane (methoxypoly(ethyleneoxy)$_{6-9}$propyltrimethoxysilane). However, $PEG_{6-9}$-silane can affect the formation of emulsions, causing excessive pigment flotation. Further, the long-term oxidative stability of $PEG_{6-9}$-silane and degradation products of ethyleneoxide derived materials have potential health effects that may be of concern in some formulations.

The utilization of modified amino acids as surface treatments for particulates, including pigments and fillers, is well-known in cosmetic and personal care technology. Examples are coated pigments and fillers with excellent skin feel and reduced potential for skin abrasion, prepared by utilizing salts of acyl amino acids such as aluminum N-myristoyl-L-glutamate (see U.S. Pat. No. 4,606,914 of Miyoshi); platy pigments with improved tactile properties, prepared by precipitation of acylamino acids such as N-lauroyllysine on the surface of talcs (see, for example, U.S. Pat. No. 5,326,392 of Miller); and skin treatments prepared by treating pigments and fillers with combinations of N-acylamino acids, N-acylamino acid salts and fatty acids (see U.S. Pat. No. 7,374,783 of Hasegawa). All of these coatings are produced by adsorbing or precipitating amino acids on particles. For the most part, these coatings are relatively hydrophobic since they are derived from N-acyl substituted amino acids in which the acyl group has six or more carbons, most often lauroyl (12 carbons). The use of particles treated with these systems is restricted to oil based color cosmetics, either anhydrous formulations or water-in-oil emulsions, because particles with adsorbed hydrophobic amino acids will not disperse in the continuous aqueous phase. The pigment phase of the finished emulsion must be dispersed in the external phase of the emulsion to allow the mass tone of the product to be similar to that achieved on the skin after application.

There are many instances in which the benefits of amino acid modified particles would be desirable in oil-in-water formulations. However, amino acids simply adsorbed onto particulates tend to destabilize oil-in-water emulsions. They also tend to coalesce dispersed oil by physically bridging on the surface of the particle by adsorption phenomena. Further, particles with adsorbed hydrophilic amino acids tend to be intrinsically unstable at water-oil interfaces since the amino acid tends to desorb from the particle, at once changing the surface characteristics of the particle and changing the aqueous environment by introducing soluble amino acids which tend to be strong zwitter-ions.

While the immobilization of enzymes and amino acids has been disclosed by Weetall (U.S. Pat. No. 3,652,761), these systems were designed for fixed-bed catalysis, and the particle dimensions are not suitable for the purpose of forming stable dispersions.

BRIEF SUMMARY OF THE INVENTION

The invention is directed to hydrophilic alkoxysilane derivatives of N-acylamino acids, N-acyl dipeptides, and N-acyl tripeptides, wherein the acyl group contains fewer than six carbon atoms.

The invention also relates to particles of a mineral, filler, or pigment having on its surface a coating of a hydrophilic alkoxysilane derivative of an N-acylamino acid, N-acyl dipeptide, or N-acyl tripeptide, wherein the acyl group contains fewer than six carbon atoms.

The invention is further directed to oil-in-water formulations containing a dispersion comprising particles of a mineral, filler, and/or pigment having on its surface a coating of a hydrophilic alkoxysilane derivative of an N-acylamino acid, N-acyl dipeptide, or N-acyl tripeptide, wherein the acyl group contains fewer than six carbon atoms.

Finally, the invention is directed to a pressed powder or color cosmetic comprising particles of a mineral, filler, and/or pigment having on its surface a coating of a hydrophilic alkoxysilane derivative of an N-acylamino acid, N-acyl dipeptide, or N-acyl tripeptide, wherein the acyl group contains fewer than six carbon atoms.

DETAILED DESCRIPTION OF THE INVENTION

The present invention is directed to alkoxysilane derivatives of N-acyl amino acids, N-acyl dipeptides, and N-acyl tripeptides, in which the number of carbon atoms in the acyl substitution is fewer than six carbons, preferably two carbons (acetyl). The N-acyl amino acid, N-acyl dipeptide, and N-acyl tripeptide is not limited, provided that the acyl substituent contains fewer than six carbon atoms. If the acyl group contains more than six carbon atoms, the resulting amino acid or di- or tripeptide becomes hydrophobic. For example, exemplary amino acids include N-acetylglycine, N-acetylproline, N-acetylhydroxyproline, and N-acetyl leucine. Exemplary dipeptides include N-acetylglycylglycine and N-acetylglycylserine, and an exemplary tripeptide is N-acetylglycylglycylglycine.

Although there is no limitation on the length of the alkoxy group, preferred alkoxy groups include methoxy and ethoxy.

Preferred compounds according to the invention contain three alkoxy groups (which may be the same or different, such as dimethoxyethoxy or diethoxymethoxy), although compounds containing two alkoxy groups are also within the scope of the invention.

The compounds of the invention are preferably alkylalkoxysilane derivatives, such as methylalkoxy, ethylalkoxy, and propylalkoxy, propylalkoxy being presently preferred. Other alkyl group lengths are also within the scope of the invention, but are not presently preferred for economic reasons. Accordingly, in preferred embodiments, the compounds are propyltrialkoxysilane derivatives of N-acyl amino acids, N-acyl dipeptides, or N-acyl tripeptides, such as propyltrimethoxysilane and propyltriethoxysilane derivatives. For example, exemplary compound according to the invention include N-acetylglycylglycylglycylglycylpropyltriethoxysilane and N-acetylglycylglycylglycylpropyltriethoxysilane.

Exemplary silane modified amino acids, which have been found to enhance dispersion of particles in aqueous phases, include:

(N-Acetylglycylpropyl)triethoxysilane

(N-Acetylglycinamidepropyl)trimethoxysilane

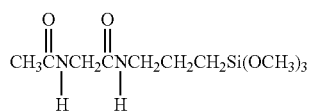

(N-Acetylleucinamidepropyl)triethoxysilane

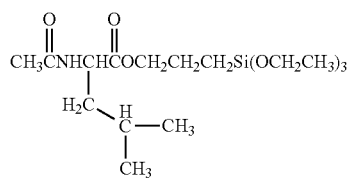

(N-Acetyl-4-hydroxyprolyl)propyltriethoxysilane

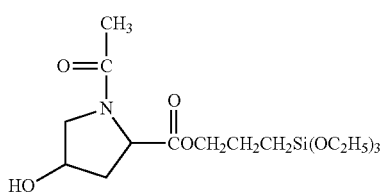

The method of preparing these materials is not critical and the compounds may be prepared by any effective method known in the art or to be developed. Preferred methods include carbodiimide coupling, resulting in amide formation, or the formation of an alkali metal salt of the amino acid and reaction with a halogenated alkylsilane, resulting in ester formation. Ester formation is advantageous because the need for strong dehydrating reagents such as carbodiimides, which tend to be skin sensitizing agents, is eliminated. For example, the compounds may be prepared by a coupling reaction between a haloalkoxysilane and the salt of the appropriate N-acyl amino acid, N-acyl dipeptide, or N-acyl tripeptide. For instance, (N-Acetylglycylpropyl)triethoxysilane may be prepared via the reaction of 3-iodopropyltriethoxysilane with N-acetylglycine.

The invention is also directed to particles (such as particles of minerals, pigments, or fillers) that have been treated with the alkoxysilane derivatives of N-acylaminoacids, N-acyl dipeptides, or N-acyl tripeptides to create relatively hydrophilic particle surfaces. In other words, the treated particles have on their surface a coating of a hydrophilic alkoxysilane derivative of an N-acyl amino acid, N-acyl dipeptide, or N-acyl tripeptide according to the invention. The modification may be performed as described by Arkles in *Chemtech*, 7(12), 766, (1977), which is herein incorporated by reference. These treated particles according to the invention wet preferentially in water, rendering the resulting pigments or fillers suitable for use in water-based formulations, including gels and oil-in-water emulsions. The covalent bonding of hydrophilic amino acids or analogous di- and tripeptides on particles provides for the formation of stable oil-water systems, especially emulsion interfacial systems, without deterioration. In order to function as stable dispersions, the treated particles of this invention preferably are no greater than about 200 microns in the largest dimension and no less than about 0.01 microns in the smallest dimension.

The particles according to the invention are particularly useful in cosmetics. Particles utilized in cosmetics include both filler materials, such as mica, talc, sericite, silica, fluorophlogopite, borosilicate flakes, alumina, and kaolin, inorganic pigments, such as iron oxides, titanium dioxide, ferric ammonium ferrocyanide, chromium oxide, chromium hydroxide, zinc oxide, and ultramarines, and organic pigments, such as carmine, and the FDA certified lakes of Red 6, Red 7, Red 21, Red 27, Red 33, Red 36, Red 40, Yellow 5, Yellow 6, Yellow 10, and Blue 1. These types of particles are meant to be exemplary, not limiting, and it is within the scope of the invention to treat other types of particles (both those useful in cosmetics and those that are not), as well.

The invention is also directed to oil-in-water formulations, such as, without limitation, concealers or foundations, containing dispersions comprising particles of a mineral, filler, and/or pigment having on its surface a coating of an alkoxysilane derivative of an N-acyl amino acid, N-acyl dipeptide, or N-acyl tripeptide according to the invention. Another potential benefit of hydrophilic amino acid modified particles (or the analogous di- and tri-peptides) is that they may contribute to skin care as natural moisturizing factors when utilized alone or in combination with unbound hydrophilic amino acids and formulated into foundations or concealers. Further, the invention is directed to pressed powder and color cosmetics, including those suitable for eye area use, containing such treated particles. The additional components of the oil-in-water formulations and cosmetics, and methods for their preparation, are well known in the art and need not be described.

The invention will now be described in conjunction with the following, non-limiting examples.

EXAMPLES

Preparation Examples

Example 1

Preparation of (N-Acetyl-glycylpropyl)triethoxysilane

A 5 L, 4-neck flask equipped with a heating mantle, a mechanical stirrer, a pot thermometer, an addition funnel, and a short Vigreux column with a distillation head connected to a nitrogen bubbler was charged with 2500 g of ethanol and 146.4 g of N-acetylglycine. This mixture was stirred at room temperature for 15 minutes. 110.5 g of potassium ethoxide were added while maintaining the pot temperature below 50° C. The mixture was heated to a pot temperature of 80° and 362.7 g of 3-iodopropyltriethoxysilane was added. Ethanol was removed by distillation until the pot temperature rose to 90° C. to 95° C. The reaction was followed by GC and heating continued for ~100 hours until less than 10% of the 3-iodopropyltriethoxysilane remained. The flask and the contents were allowed to cool to room temperature and then filtered to give a clear to slightly hazy solution with 25-30% solids. A sample of solution was stripped of solvent at 120° C. and 1 mm vacuum to remove all solvents and unreacted starting materials. The product was purified by wiped film distillation at 190° C. at 0.5 mm. IR and NMR results were consistent with the target structure.

Example 2

Preparation of
(N-Acetyl-4-hydroxyprolyl)propyltriethoxysilane

A 5 L, 4-neck flask equipped with a heating mantle, a mechanical stirrer, a pot thermometer, an addition funnel, and a short Vigreux column with a distillation head connected to a nitrogen bubbler was charged with 2500 g of ethanol and 432.9 g of N-acetylhydroxyproline. This mixture was stirred at room temperature for 15 minutes. 220.9 g of potassium ethoxide were added while maintaining the pot temperature below 40° C. The pot temperature was slowly heated to 80° C. and 500 ml of ethanol were removed and discarded. At a pot temperature of 80° C., 31.1 g of potassium iodide and 602 g of chloropropyltriethoxysilane were added. An additional 500 ml of ethanol was removed by distillation and retained. The pot temperature gradually rose from 80° C. to 90° C. during removal of ethanol. The reaction was followed by GC, and heating was continued until less than 5% of the 3-chloropropyltriethoxysilane remained. The retained ethanol was charged back to the flask and the contents were allowed to cool to room temperature. The mixture was filtered to give ~3 kg of a clear to slightly hazy amber solution with 25-30% solids. The density of the solution at 25° C. was 0.87 g/cm³. A sample of solution was stripped of solvent at 60° C. and 1 mm vacuum to give gel-like solids. IR and NMR results were consistent with the target structure.

Example 3

Preparation of
(N-Acetyl-leucinamidepropyl)triethoxysilane

A 1 L, 4-neck flask equipped with a heating mantle, a magnetic stirrer, a pot thermometer, an addition funnel, and a dry-ice condenser connected to a nitrogen bubbler was charged with 125 ml of dimethylformamide and 25 g of N-acetylleucine. This mixture was stirred at room temperature for 15 minutes. 14.9 g of dicyclohexylcarbodiimide in 10 portions were added. Pot temperature rose 10° C. The mixture was stirred for 60 minutes and the pot temperature returned to 24° C. 32 g of 3-aminopropyltriethoxysilane was added over 45 minutes as the pot temperature rose 15° C. The mixture was stirred for an additional 4 hours. The flask was heated to 40° C. and the dimethylformamide was removed under vacuum. 300 ml of toluene were added and the mixture was heated to 40° C. and then allowed to stir overnight without heating. The mixture was filtered. The solids were washed with 100 ml of toluene and the volatiles were stripped from the combined filtrates to give the product as a pale yellow solid. IR and NMR results were consistent with the target structure. The product formed a 13% solution in ethanol after warming to 30° C. with a density of 0.763.

Example 4

Preparation of
(N-Acetylglycinamidepropyl)trimethoxysilane

A 3 L, 4-neck flask equipped with a heating mantle, a mechanical stirrer, a pot thermometer, an addition funnel, and a dry-ice condenser connected to a nitrogen bubbler was charged with 300 ml of dimethylformamide and 58.5 g of acetylglycine. This mixture was stirred at room temperature for 20 minutes. 56.1 g of dicyclohexylcarbodiimide in 10 portions were added, and the pot temperature rose 12° C. The mixture was stirred for 60 minutes and the pot temperature returned to 25° C. 44.8 g of 3-aminopropyltrimethoxysilane were added over 45 minutes as the pot temperature rose 20° C. The mixture was stirred for an additional 4 hours. The flask was heated to 40° C. and the dimethylformamide was removed under vacuum. 400 ml of THF were added to the pot and that mixture was heated to 40° C. and then allowed to stir overnight without heating. The mixture was filtered at room temperature. The solids were washed with 100 ml of THF and the volatiles were stripped from the combined filtrates to give the product as a pale yellow solid. IR and NMR results were consistent with the target structure. The product formed a 5% solution in methanol at 25° C. with a density of 0.799.

Preparation of Particles and Analysis

Preparation of Treated Particles

Example 5

Preparation of Treated Yellow Iron Oxide 2 grams of (N-acetyl-4-hydroxyprolyl)propyltriethoxysilane (prepared in Example 2) were added to 2000 ml of an 80% isopropanol/20% distilled water solution with stirring. The silane was allowed to hydrolyze at ambient conditions for 2 hours. 100 grams of yellow iron oxide were added and stirring continued for one hour. The suspension was filtered and the filtrate was heated to 80° C. for 4 hours. The resulting powder was milled using a hammer mill through a 0.027" screen.

Example 6

Preparation of Treated Red Iron Oxide, Black Iron Oxide, and Titanium Dioxide 2 grams of (N-acetyl-4-hydroxyprolyl)propyltriethoxysilane (prepared in Example 2) were sprayed onto 100 grams of dry red iron oxide under agitation in a tumbling mixer. The powder was agitated for one hour at ambient conditions and then heated to 80° C. for four hours. After cooling, the treated powder was deagglomerated by milling with a hammer mill through a 0.035" screen. Black iron oxide and titanium dioxide treated particles were prepared in an analogous fashion.

Example 7

Preparation of Treated Sericite 2 grams of (N-acetyl-4-hydroxyprolyl)propyltriethoxysilane (prepared in Example 2) were sprayed onto to 100 grams of sericite under agitation in a tumbling mixer. The powder was agitated for one hour at ambient conditions and then heated to 80° C. for four hours. After cooling, the treated powder was milled using a hammer mill through a 0.067" screen.

Analysis of Treated Pigment Particles

The four treated pigments (yellow iron oxide, red iron oxide, black iron oxide, and titanium dioxide) were analyzed and compared with a variety of comparative materials in order to determine the effect of surface modification on the pigment particles.

Aqueous Dispersion (Visual):

0.3 grams of each treated pigment were added to 15 ml deionized water. Behavior was observed without stirring and the results tabulated in Table 1.

TABLE 1

| Visual Evaluation of Treated Pigment Particles | | | | |
|---|---|---|---|---|
| | Yellow Iron Oxide | Red Iron Oxide | Black Iron Oxide | Titanium Dioxide |
| control (untreated) | wets, falls to bottom | falls to bottom | falls to bottom | bloom |
| PEG$_{6-9}$ Silane | self disperses | self disperses | slight bloom | self disperses |
| PEG-8 | wets slowly; falls to bottom; slight bloom | wets slowly; falls to bottom; slight bloom | wets slowly; falls to bottom | wets slowly; falls to bottom; slight bloom |
| Aminopropyl Silane | wets slowly bloom | blooms 50% | slight bloom; settles | wets slowly; slight bloom |
| Na2 Carboxyethylsilanetriol | self disperses | self disperses | sl bloom | self disperses |
| Na Propionate | wets slowly; very slight bloom | wets slowly; settles | wets slowly; settles | wets slowly; very slight bloom |
| N-Acetyl Hydroxyproline | falls to bottom | falls to bottom | falls to bottom | falls to bottom |
| N-Acetyl Hydroxyprolyl propyltriethoxysilane | self disperses | self disperses | slight bloom | self disperses |

It can be seen in Table 1 that all of the pigments with hydrophilic modification deagglomerated and dispersed without stirring to some extent. PEG$_{6-9}$ silane (methoxy (polyethyleneoxy)$_{6-9}$propyltrimethoxysilane), sodium carboxyethylsilanetriol, and (N-acetylhydroxyprolyl)propyltriethoxysilane treated pigments dispersed completely, some particles remaining in suspension for over one month.

Deposition of the polar compounds alone on the pigment surfaces did not produce the instant dispersion effect that results from surface treatment with silanes having the polar compounds as a functional group. The dry treated pigments were de-agglomerated to some extent due to the milling steps in the treatment process, but the effect was negated by particle size reduction steps of all samples used for dispersion testing. The greater surface area can actually appear to slow the wetting process, but the results of the viscosity tests described below show that wetting of the treated particles improved compared to the untreated pigments. The dramatic dispersion of the hydrophilic treatments seen in visual evaluation was confirmed by the quantitative measurements.

Dispersion Viscosity (Butylene Glycol):

Dispersions of the pigments were prepared by wetting in butylene glycol with stirring for one hour, followed by three passes over a three roll mill. Viscosity was measured using a Brookfield viscometer using standard spindles at 20 RPM. Different spindle sizes were used in different viscosity ranges. The results are tabulated in Table 2. Lower viscosity at equal concentration and degree of dispersion (particle size) indicates better wetting.

TABLE 2

Dispersion Viscosity of Treated Pigment Particles

| Treatment | Pigment, % in Butylene Glycol | | | |
|---|---|---|---|---|
| | Yellow Iron Oxide 45% | Red Iron Oxide 50% | Black Iron Oxide 50% | Titanium Dioxide 50% |
| control (untreated) | 73,400 cps (spindle #7) | 24,500 cps (spindle #6) | 10,950 cps (spindle #6) | 11,150 cps (spindle #6) |
| PEG$_{6-9}$ Silane | 1,610 cps (spindle #3) | 2,100 cps (spindle #4) | 3,970 cps (spindle #4) | 12,150 cps (spindle #6) |
| Aminopropyl Silane | 675 cps (spindle #3) | 4,100 cps (spindle #4) | 9,000 cps (spindle #4,5) | 4,700 cps (spindle #4) |
| Na Carboxyethyl-silanetriol | 540 cps (spindle #3) | 2,690 cps (spindle #4) | 6,500 cps (spindle #4,5) | 415 cps (spindle #3) |
| N-Acetyl Hydroxyprolyl propyltriethoxysilane | 520 cps (spindle #3) | 3,120 cps (spindle #4) | 5,940 cps (spindle #4,5) | 2,870 cps (spindle #3) |

It can be seen that all of the hydrophilic treated pigments improved wetting and dispersion in butylene glycol relative to the untreated pigment, except, surprisingly, PEG$_{6-9}$ silane on titanium dioxide. (N-acetyl-hydroxyprolyl)propyltriethoxysilane treated pigments performed comparably to the other hydrophilic treatments. Dispersion viscosity measurements indicated that PEG$_{6-9}$ silane, sodium carboxyethylsilanetriol, and (N-acetyl-hydroxyprolyl)propyltriethoxysilane treated iron oxides exhibited the best wetting. Sodium carboxyethylsilanetriol and (N-acetyl-hydroxyprolyl)propyltriethoxysilane treatments were the most effective treatment for titanium dioxide.

Formulation and Cosmetics Preparation and Analysis

Example 8

Preparation and Analysis of Oil-In-Water Concealers

Five anionic oil-in-water emulsion concealers containing 20% pigment and filler were prepared using the components shown in Table 3. One formulation was prepared using pigments treated with (N-acetyl-4-hydroxyprolyl)propyltriethoxysilane (as prepared in Example 2), and three comparative formulations were prepared using pigments treated with PEG$_{6-9}$ silane, aminopropylsilane, or sodium carboxyethylsilanetriol. A fifth formulation was prepared as a control using untreated pigments. In each case, water phase ingredients were added in order to the finishing beaker while homogenizing at low speed. Following Veegum addition, the phase was heated to 85-90° C. for 15 minutes, then other additions were performed at 75° C. The oil phase ingredients were combined and stirred at 75-80° C. until homogenous. The oil phase was added to the water phase with homogenization.

TABLE 3

Formulation for Oil-in-Water Concealer

| Ingredient | INCI* Name | % by weight |
|---|---|---|
| Water Phase | | |
| Deionized Water | | 50.37 |
| Tween 60 | Polysorbate 60 | 0.10 |
| Laponite XLG | Sodium Lithium Magnesium Silicate | 0.30 |
| Veegum reg | Magnesium Aluminum Silicate | 0.70 |
| Titanium Dioxide | Titanium Dioxide | 16.00 |
| Yellow Iron Oxide | Iron Oxides | 1.60 |
| Red Iron Oxide | Iron Oxides | 0.60 |
| Black Iron Oxide | Iron Oxides | 0.16 |

TABLE 3-continued

Formulation for Oil-in-Water Concealer

| Ingredient | INCI* Name | % by weight |
|---|---|---|
| Talc | Talc | 1.64 |
| Butylene Glycol | | 6.00 |
| CMC7H3SF (Aqualon) | Cellulose Gum | 0.10 |
| Tween 60 (Croda) | Polysorbate 60 | 0.40 |
| Methylparaben | | 0.25 |
| Amphisol K (DSM) | Potassium Cetyl Phosphate | 2.00 |
| Oil Phase | | |
| DE 12 (Gelest) | Polydiethylsiloxane | 12.00 |
| Ceraphyl 368 (ISP) | Ethylhexyl Palmitate | 5.00 |
| Span 60 (Croda) | Sorbitan Stearate | 1.00 |
| Cerasynt SD (ISP) | Glyceryl Stearate | 1.50 |

TABLE 3-continued

Formulation for Oil-in-Water Concealer

| Ingredient | INCI* Name | % by weight |
|---|---|---|
| Propylparaben | | 0.10 |
| Glydant (Lonza) | DMDM Hydantoin | 0.18 |
| | | 100.00 |

*INCI = International Nomeclature of Cosmetic Ingredients

Performance of the treated pigments in the formulations was analyzed visually. Dispersion quality was evaluated by the presence or absence of undispersed color, detected by pressing a drop of the finished emulsion between two microscope slides and checking for spots of color. Time required to wet the particles was used to compare ease of wetting. "Rapid" means pigment dispersion and color development commenced immediately after addition of the powders to the water phase. "Slow" refers to the presence of unwet agglomerates even after five minutes of mixing. "Intermediate" refers to a delay of 45-90 seconds between pigment addition and disappearance of dry particles. Color development (intensity) in the final product and presence or absence of color flotation during processing were observed and photographed for later analysis. Viscosity and emulsion stability of the final products were also monitored. Data for untreated pigments and those having control treatments are compared against pigments treated with (N-acetyl hydroxyprolyl)propyltriethoxysilane and the results are shown in Table 4.

TABLE 4

Analysis of Concealer Formulations

| | Parameter | | | |
|---|---|---|---|---|
| Treatment | Dispersion | Color development[1] (Intensity) | Wetting | Flotation |
| control (untreated) | undispersed pigment | 1 | slow | white |
| PEG$_{6-9}$ Silane | complete | 4 | rapid | white/yellow/black |
| Aminopropyl Silane | undispersed TiO$_2$ | 2 | slow | white |
| Na Carboxyethylsilanetriol | complete | 5 | rapid | yellow > 60° C. |
| N-Acetyl Hydroxyprolyl propyltriethoxysilane | complete | 3 | intermediate | none |

[1]On a scale of 1 to 5, 1 being the lowest

The data clearly demonstrate the hydrophilicity and dispersibility in water of the (N-acetyl-hydroxyprolyl)propyltriethoxysilane treated pigments.

Surprisingly, (N-acetyl-4-hydroxyprolyl)propyltriethoxysilane treatment resulted in the most consistent wetting of the different pigments. The formula containing (N-acetyl-4-hydroxyprolyl)propyltriethoxysilane treated pigments exhibited good dispersion with no visible agglomerates and none of the color flotation that usually indicates poor wetting of an individual colorant. The formula spread evenly over the skin to leave a comfortable layer on the delicate under-eye area that hid dark circles and other imperfections. The emulsion was stable under accelerated aging and long term testing.

Interaction of the treated surfaces with other raw materials may be the cause of the variable results observed with the other treatments in the actual formulation. Surface activity of the PEG group of the PEG$_{6-9}$ silane may affect the formation of the emulsion, causing excessive pigment flotation, and appears to influence wetting of some thickening agents. The anionic nature of sodium carboxyethylsilanetriol does stabilize pigment dispersions, but the effect of the added electrolyte on other raw materials, particularly gellants, may be the cause of emulsion instability or color flotation. Accordingly, the inventive materials provide results that are not achieved by prior art materials.

Example 9

Preparation and Analysis of Pressed Powder Foundation

A pressed powder foundation was prepared using the components shown in Table 5 by combining the powder phase in a tumbling mixer equipped with a high speed agitator. When homogenous, the oils were combined and added to the batch with agitation until dispersed. The powder was pressed into suitable pans at 750 psi. The product exhibited excellent affinity for the skin, applying smoothly with a soft, silky feel to give full, yet natural looking coverage that lasted all day.

TABLE 5

Formulation for Pressed Powder Foundation

| Ingredient | Surface treatment | % |
|---|---|---|
| Powder Phase | | |
| Mica | (N-Acetyl-hydroxyprolyl)propyltriethoxysilane | 20.00 |
| Yellow Iron Oxide | (N-Acetyl-hydroxyprolyl)propyltriethoxysilane | 2.00 |

TABLE 5-continued

Formulation for Pressed Powder Foundation

| Ingredient | Surface treatment | % |
|---|---|---|
| Red Iron Oxide | (N-Acetyl-hydroxyprolyl)propyltriethoxysilane | 0.80 |
| Black Iron Oxide | (N-Acetyl-hydroxyprolyl)propyltriethoxysilane | 0.35 |
| Talc | (N-Acetyl-hydroxyprolyl)propyltriethoxysilane | 55.84 |
| Zinc Stearate | | 3.00 |
| Nylon -12 | | 5.00 |
| Benzoic Acid | | 0.10 |
| Oil Phase | | |
| Octyldodecyl Stearate | | 2.50 |
| Polydiethylsiloxane | | 1.50 |
| | | 100.00 |

Example 10

Pressed Powder Eye Shadow

A pressed powder eye shadow was prepared using the components shown in Table 6 by combining the powder phase in a tumbling mixer equipped with a high speed agitator. When homogenous, the oils were combined and added to the batch with agitation until dispersed. The powder was pressed into suitable pans at 850 psi. The product applied smoothly with a soft, silky feel to the delicate eye area. Due to the affinity of the (N-acetyl-4-hydroxyprolyl)propyltriethoxysilane treated pigments for the skin, the eye shadow exhibited long wear and resistance to creasing.

TABLE 6

Pressed Powder Eye Shadow Formulation

| Ingredient | Surface Treatment | % |
|---|---|---|
| Powder Phase | | |
| Mica | (N-Acetyl-hydroxyprolyl)propyltriethoxysilane | 30.00 |
| Yellow Iron Oxide | (N-Acetyl-hydroxyprolyl)propyltriethoxysilane | 3.00 |
| Red Iron oxide | (N-Acetyl-hydroxyprolyl)propyltriethoxysilane | 3.00 |
| Black Iron Oxide | (N-Acetyl-hydroxyprolyl)propyltriethoxysilane | 4.00 |
| Talc | (N-Acetyl-hydroxyprolyl)propyltriethoxysilane | 47.90 |
| Zinc Stearate | | 3.00 |
| Nylon-12 | | 5.00 |
| Benzoic Acid | | 0.10 |
| Oil Phase | | |
| Octyldodecyl Stearate | | 2.50 |
| Polydiethylsiloxane | | 1.50 |
| | | 100.00 |

Example 10

Preparation and Analysis of Eyeliner

A water based eyeliner was prepared by dispersing (N-acetyl-4-hydroxyprolyl)propyltriethoxysilane treated black iron oxide in the water phase of the emulsion with only low speed homogenization to give fine pigment particle size with full color development. The eyeliner drew a fine line behind the eye lashes that adhered well throughout the day. The formulation of the eyeliner is shown in Table 7.

TABLE 7

Formulation of Eyeliner

| Ingredient | % |
|---|---|
| Deionized Water | 69.49 |
| Butylene Glycol | 6.00 |
| Methylparaben | 0.30 |
| TrisAmino (Dow) [Tromethamine] | 1.00 |
| Deionized Water | 4.00 |
| Shellac (Mantrose-Haeuser) | 1.00 |
| Hydroxyethylcellulose | 0.50 |
| Black Iron Oxide treated with (N-acetyl-4-hydroxyprolyl)propyltriethoxysilane | 10.00 |
| Wax Phase | |
| White Beeswax | 4.00 |
| Carnauba Wax | 0.50 |
| Cetyl Alcohol | 1.25 |
| Sorbitan Stearate | 1.00 |
| Hydrogenated Polyisobutene | 0.50 |
| Propylparaben | 0.10 |
| DMDM Hydantoin | 0.36 |
| | 100.00 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A particle of a mineral, filler, or pigment having on its surface a coating of a hydrophilic alkoxysilane derivative of an N-acylamino acid, N-acyl dipeptide, or N-acyl tripeptide, wherein the acyl group contains fewer than six carbon atoms, and wherein the derivative forms a covalent bond with a surface of the particle via an oxane bridge between a silicon atom in the silane and the particle, and wherein the covalent bonding provides for the formation of stable oil-water systems.

2. The particle according to claim 1, wherein the acyl group is acetyl.

3. The particle according to claim 1, wherein the alkoxy group is selected from the group consisting of methoxy and ethoxy.

4. The particle according to claim 1, wherein the derivative is a propyltrialkoxysilane derivative.

5. The particle according to claim 1, wherein the derivative is (N-acetylglycylpropyl)triethoxysilane.

6. The particle according to claim 1, wherein the derivative is (N-acetylglycinamidepropyl) trimethoxysilane.

7. The particle according to claim 1, wherein the derivative is (N-acetylleucinamidepropyl) triethoxysilane.

8. The particle according to claim 1, wherein the derivative is (N-acetylhydroxyprolyl)propyltriethoxysilane.

9. The particle according to claim 1, wherein the particle has a dimension no greater than about 200 microns in a largest dimension and no less than about 0.01 microns in the smallest dimension.

10. An oil-in-water formulation containing a dispersion comprising particles of a mineral, filler, and/or pigment having on its surface a coating of a hydrophilic alkoxysilane derivative of an N-acylamino acid, N-acyl dipeptide, or N-acyl tripeptide, wherein the acyl group contains fewer than six carbon atoms, and wherein the derivative forms a covalent bond with a surface of the particle via an oxane bridge between a silicon atom in the silane and the particle.

11. A pressed powder or color cosmetic comprising particles of a mineral, filler, and/or pigment having on its surface a coating of a hydrophilic alkoxysilane derivative of an N-acylamino acid, N-acyl dipeptide, or N-acyl tripeptide, wherein the acyl group contains fewer than six carbon atoms, and wherein the derivative forms a covalent bond with a surface of the particle via an oxane bridge between a silicon atom in the silane and the particle.

* * * * *